US010030188B2

United States Patent
Jiang et al.

(10) Patent No.: US 10,030,188 B2
(45) Date of Patent: *Jul. 24, 2018

(54) NANO-HYBRID LUBRICANT AND METHOD THEREOF, AND OIL-BASED DRILLING FLUID

(71) Applicant: CHINA UNIVERSITY OF PETROLEUM (BEIJING), Beijing (CN)

(72) Inventors: Guancheng Jiang, Beijing (CN); Shuanglei Peng, Beijing (CN); Yinbo He, Beijing (CN); Deli Gao, Beijing (CN); Lili Yang, Beijing (CN); Fan Liu, Beijing (CN); Xinliang Li, Beijing (CN); Zhengqiang Deng, Beijing (CN); Haifang Sun, Beijing (CN); Liexiang Han, Beijing (CN)

(73) Assignee: China University of Petroleum (Beijing) (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/466,036

(22) Filed: Mar. 22, 2017

(65) Prior Publication Data
US 2017/0349802 A1     Dec. 7, 2017

(30) Foreign Application Priority Data
Jun. 1, 2016   (CN) .......................... 2016 1 0380561

(51) Int. Cl.
| | | |
|---|---|---|
| C09K 8/32 | (2006.01) | |
| C07D 303/40 | (2006.01) | |
| C10M 103/00 | (2006.01) | |
| C10M 105/62 | (2006.01) | |
| C10M 105/60 | (2006.01) | |

(52) U.S. Cl.
CPC .............. C09K 8/32 (2013.01); C07D 303/40 (2013.01); C10M 103/00 (2013.01); C10M 105/60 (2013.01); C10M 105/62 (2013.01); C09K 2208/10 (2013.01); C09K 2208/34 (2013.01); C10M 2201/003 (2013.01); C10M 2215/041 (2013.01)

(58) Field of Classification Search
CPC .. C09K 8/32; C09K 2208/10; C09K 2208/34; C07D 303/40; C10M 103/00; C10M 105/60; C10M 105/62; C10M 2201/003; C10M 2215/041; C10M 177/00; C10M 103/02
USPC ....................................................... 507/131
See application file for complete search history.

(56) References Cited

U.S. PATENT DOCUMENTS

| | | | |
|---|---|---|---|
| 4,501,672 A | 2/1985 | Connell | |
| 7,772,165 B2 | 8/2010 | Knox | |
| 8,222,455 B2* | 7/2012 | Knox | A61K 8/02 166/280.2 |
| 9,365,762 B1 | 6/2016 | Jiang | |
| 9,481,822 B1 | 11/2016 | Jiang | |
| 9,528,042 B1 | 12/2016 | Jiang | |
| 2011/0059871 A1 | 3/2011 | Tour et al. | |
| 2012/0245058 A1* | 9/2012 | Monteiro | C09K 8/032 507/110 |
| 2015/0361323 A1* | 12/2015 | Gamage | C09K 8/035 166/305.1 |

FOREIGN PATENT DOCUMENTS

| | | |
|---|---|---|
| CN | 102015958 A | 4/2011 |
| CN | 102199417 A | 9/2011 |
| CN | 103980869 A | 8/2014 |
| CN | 104531106 A | 4/2015 |

(Continued)

OTHER PUBLICATIONS

First Office Action from Chinese Application No. 201610381991.1 dated Feb. 4, 2017.

(Continued)

*Primary Examiner* — Frances Tischler
(74) *Attorney, Agent, or Firm* — Calfee, Halter & Griswold LLP (57) ABSTRACT

The present invention relates to the well drilling field in petroleum industry, in particular to a nano-hybrid lubricant and method thereof, and oil-based drilling fluid. The lubricant comprises: graphite oxide and a biquaternary ammonium salt compound of which the cation part is represented by formula (1). The present invention also provides a method for preparation of the lubricant and an oil-based drilling fluid containing the lubricant. The lubricant provided in the present invention can be comprehended as a nano-hybrid material. Thus, oil-based drilling fluids that contain the lubricant provided in the present invention have lower lubrication coefficient and excellent lubricating property without or with little negative impact on rheological property of the oil fluid, and the lubricant provided in the present invention has excellent thermostability thus suitable for use in operation at a high temperature.

formula (1)

$$R^3 \diagdown \underset{\underset{R^2}{|}}{\overset{\overset{R^2\ R^1}{|}}{N^+}} \diagdown \underset{OH}{\diagdown} \diagdown \underset{\underset{R^2}{|}}{\overset{\overset{R^1\ R^2}{|}}{N^+}} \diagdown R^3$$

17 Claims, 2 Drawing Sheets

(56) References Cited

FOREIGN PATENT DOCUMENTS

| | | |
|---|---|---|
| CN | 104893691 A | 9/2015 |
| CN | 105441038 A | 3/2016 |
| CN | 105623626 A | 6/2016 |
| CN | 105647489 A | 6/2016 |
| WO | 2015147852 A1 | 10/2015 |

OTHER PUBLICATIONS

First Office Action from Chinese Application No. 201610380561.8 dated Mar. 3, 2017.

* cited by examiner

NANO-HYBRID LUBRICANT AND METHOD THEREOF, AND OIL-BASED DRILLING FLUID

CROSS REFERENCE TO RELATED APPLICATIONS

This application claims priority to Chinese Application No. 201610380561.8, filed on Jun. 1, 2016, entitled "Nano-Hybrid Lubricant, Method and Use Thereof, and Oil-Based Drilling Fluid and Use Thereof", which is specifically and entirely incorporated by reference.

FIELD OF THE INVENTION

The present invention relates to the well drilling field in petroleum industry, in particular to a nano-hybrid lubricant and method thereof, and oil-based drilling fluid.

BACKGROUND OF THE INVENTION

In a well drilling process, the rotating drilling stem inevitably comes into contact with the casing or rock well wall and thereby produces friction force, resulting in increased torque, decreased drilling rate, and abrasion of the drilling tool. If the friction force is too high, complex downhole conditions, such as difficulty in tripping operation, caving, or jamming of drilling tool, etc. may occur. Hence, often a lubricant has to be added into the drilling fluid to improve the lubricating property of the system during well drilling, reduce frictional resistance in the drilling process, prevent the occurrence of complex downhole conditions (e.g., jamming of drilling tool), and ensure safe and quick well drilling.

Presently, there are great varieties of lubricants for water-based drilling fluids, and these lubricants are widely applied, while researches on lubricants for oil-based drilling fluids and products of such lubricants are rare, owing to the excellent self-lubricating property of oil-based drilling fluids. However, as the drilling depth and difficulties increase, especially as more and more extra-deep wells, extended reach wells, horizontal wells and cluster wells are drilled, even oil-based drilling fluids can't solve the problem of high torque and severe wear in the drilling process; consequently, downhole accidents, such as caving and jamming of drilling tool, etc. occur frequently.

SUMMARY OF THE INVENTION

The object of the present invention is to provide a nano-hybrid lubricant with perfect lubricating property applicable to oil-based drilling fluids and method thereof, and oil-based drilling fluid.

To attain the object described above, the present invention provides a lubricant comprising graphite oxide and a biquaternary ammonium salt compound of which the cation part is represented by formula (1):

formula (1)

wherein, each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; each $R^3$ group is independently selected from H, C1-C20 alkyl, and C1-C20 hydroxyalkyl.

The present invention further provides a method for preparation of a lubricant, which comprises:

in the presence of an acid, subjecting one or more of amine compounds represented by formula (3), one or more of epoxy compounds represented by formula (4) and graphite oxide to have a contact reaction in a solvent, wherein:

wherein each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; $R^3$ group is selected from H, C1-C20 alkyl, and C1-C20 hydroxyalkyl; X is halogen, preferably is Cl or Br.

The present invention further provides an oil-based drilling fluid containing the above mentioned lubricant.

The lubricant provided in the present invention can be comprehended as a nano-hybrid material. Thus, oil-based drilling fluids that contain the lubricant provided in the present invention have lower lubrication coefficient and excellent lubricating property without or with little negative impact on rheological property of the oil fluid, and the lubricant provided in the present invention has excellent thermostability thus suitable for use in operation at a high temperature.

BRIEF DESCRIPTION OF DRAWINGS

The accompanying drawings are provided here to facilitate further understanding on the present invention, and constitute a part of this document. They are used in conjunction with the following embodiments to explain the present invention, but shall not be comprehended as constituting any limitation to the present invention. In the figures.

DETAILED DESCRIPTION OF THE EMBODIMENTS

Hereunder some embodiments of the present invention will be detailed. It should be appreciated that the embodiments described here are only provided to describe and explain the present invention, but shall not be deemed as constituting any limitation to the present invention.

The ends points and any value in the ranges disclosed in the present invention are not limited to the exact ranges or values. Instead, those ranges or values shall be comprehended as encompassing values that are close to those ranges or values. For numeric ranges, the end points of the ranges, the end points of the ranges and the discrete point values, and the discrete point values can be combined to obtain one or more new numeric ranges, which shall be deemed as having been disclosed specifically in this document.

The present invention provides a lubricant comprising graphite oxide and a biquaternary ammonium salt compound of which the cation part is represented by formula (1):

According to the present invention, to obtain a composition that has better lubricating property, lower impact on the rheological property of drilling fluid, and higher thermostability, preferably, in the formula (1), each $R^1$ group is independently selected from H, hydroxyl, halogen, C1-C4 alkyl, C1-C4 alkoxy, and C1-C4 hydroxyalkyl; each $R^2$ group is independently selected from H and C1-C4 alkyl; each $R^3$ group is independently selected from H, C1-C15 alkyl, and C1-C15 hydroxyalkyl.

More preferably, each $R^1$ group is independently selected from H, hydroxyl, methyl, ethyl, methoxy, ethyoxy, hydroxymethyl, and hydroxyethyl; each $R^2$ group is independently selected from H, methyl, ethyl, n-propyl, and n-butyl; each $R^3$ group is independently selected from H, methyl, ethyl, n-propyl, n-butyl, n-pentyl, n-hexyl, n-heptyl, n-octyl, n-nonyl, n-decyl, hendecyl, and dodecyl.

Further preferably, each $R^1$ group is independently selected from H, methyl and ethyl; each $R^2$ group is independently selected from H, methyl, ethyl, n-propyl, and n-butyl; each $R^3$ group is independently selected from ethyl, n-propyl, n-butyl, n-pentyl, n-hexyl, n-heptyl, n-octyl, n-nonyl, and n-decyl.

Optimally, each $R^1$ group is H; each $R^2$ group is independently selected from methyl and ethyl; each $R^3$ group is formula (1)

wherein, each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; each $R^3$ group is independently selected from H, C1-C20 alkyl, and C1-C20 hydroxyalkyl.

In the present invention, for example, the halogen comprises: F, Cl, Br, and I, etc.

For example, the C1-C6 alkyl may comprise: methyl, ethyl, n-propyl, isopropyl, n-butyl, isobutyl, sec-butyl, tert-butyl, n-pentyl, isopentyl, and n-hexyl, etc.

For example, the C1-C6 alkoxy may comprise: methoxy, ethoxy, n-propoxy, isopropoxy, n-butoxy, isobutoxy, sec-butoxy, tert-butoxy, n-pentyloxy, isopentyloxy, and n-hexyloxy, etc.

For example, the C1-C6 hydroxyalkyl may comprise: hydroxymethyl, hydroxyethyl, hydroxylpropyl, hydroxylbutyl, hydroxylamyl, and hydroxylhexyl, etc.

For example, the C1-C20 alkyl may comprise: methyl, ethyl, n-propyl, isopropyl, n-butyl, isobutyl, sec-butyl, tert-butyl, n-pentyl, isopentyl, n-hexyl, n-heptyl, n-octyl, n-nonyl, n-decyl, hendecyl (i.e., n-hendecyl), dodecyl (i.e., n-dodecyl), tridecyl (i.e., n-tridecyl), tetradecyl (i.e., n-tetradecyl), pentadecyl (i.e., n-pentadecyl), hexadecyl (i.e., n-hexadecyl), heptadecyl (i.e., n-heptadecyl), octodecyl (i.e., n-octodecyl), nonadecyl (i.e., n-nonadecyl), eicosyl (i.e., n-eicosyl), etc.

For example, the C1-C20 hydroxyalkyl may comprise: hydroxymethyl, hydroxyethyl, hydroxylpropyl, hydroxylbutyl, hydroxylamyl, hydroxylhexyl, hydroxylheptyl, hydroxyloctyl, hydroxylnonyl, hydroxyldecyl, hydroxylhendecyl, hydroxyldodecyl, hydroxyltridecyl, hydroxyltetradecyl, hydroxylpentadecyl, hydroxylhexadecyl, hydroxylheptadecyl, hydroxyloctodecyl, hydroxylnonadecyl, and hydroxyleicosyl, etc.

independently selected from ethyl, n-propyl, n-butyl, n-pentyl, n-hexyl, n-heptyl, n-octyl, n-nonyl, and n-decyl.

In a preferred embodiment of the present invention, the cation part of the biquaternary ammonium salt compound is selected from one or more of cations represented by the following formulae:

Formula (1-1)

Formula (1-2)

Formula (1-3)

Formula (1-4)

Formula (1-5)

Formula (1-6)

Formula (1-7)

Formula (1-5-1)

Formula (1-6-1)

Formula (1-7-1)

There is no particular restriction on the anion part of the biquaternary ammonium salt compound in the present invention; namely, the anion may be any conventional anion in the art; however, preferably, the anion part of the biquaternary ammonium salt compound is selected from one or more of Cl⁻, Br⁻, and I⁻, and more preferably is Cl⁻.

In a preferred embodiment of the present invention, the biquaternary ammonium salt compound is selected from one or more of compounds represented by the following formulae:

Formula (1-1-1)

Formula (1-2-1)

Formula (1-3-1)

Formula (1-4-1)

According to the present invention, the graphite oxide and the biquaternary ammonium salt compound contained in the lubricant may exist at positions in any form in relation to each other; namely, they can exist in a separated from or in any hybrid form; however, to obtain a lubricant that has a better lubricating effect, preferably the biquaternary ammonium salt compound adheres to the surface of the graphite oxide; more preferably, the biquaternary ammonium salt compound also adheres to the graphite oxide between layers, so that the biquaternary ammonium salt compound and the graphite oxide form an organic-inorganic hybrid material, and the lubricant may be deemed as a nano-hybrid lubricant. In such a case, the surface of inorganic nanometer graphite oxide is wrapped by a layer of organic biquaternary ammonium salt, i.e., the biquaternary ammonium salt compound is distributed on the surface and between the layers of the graphite oxide; thus, the long alkyl chain provided by the biquaternary ammonium salt compound is highly compatible with oil, and thereby the obtained lubricant can be well dispersed in the oil-based drilling fluid, and the biquaternary ammonium salt part that has positive charge on the biquaternary ammonium salt compound can be well adsorbed to the drilling stem or well wall; the graphite oxide may have inter-layer gliding under very low shearing stress and thereby attain an excellent lubricating effect owing to its natural laminar structure; in addition, the graphite oxide may fill up the uneven surface of drilling stem or well wall, so that the contact surface is integral and smooth. Therefore, by virtue of the combined action of the organic part and inorganic part of the lubricant provided in the present invention, the lubricant can greatly decrease the friction coefficient (equivalent to lubrication coefficient) of oil-based drilling fluid, reduce complex downhole conditions such as abrasion of drilling tool, and jamming of drilling tool, etc., and ensure safe and quick well drilling.

In a particularly preferred embodiment of the present invention, the biquaternary ammonium salt compound part is linked with the graphite oxide in the form of a modifying group, of which the cation part is represented by formula (2):

Formula (2)

The groups in the formula (2) are groups as defined above. It is seen that the modifying group is linked to the graphite oxide via the link with O indicated by a dotted line in the middle.

More preferably, the modifying group formed by the biquaternary ammonium salt compound is linked to the outer edge of the graphite oxide. The main reason is that the outer edge of graphite oxide has more aggregated carboxyl groups and hydroxyl groups, which are suitable to react with hydroxyl in the biquaternary ammonium salt compound to obtain graphite oxide linked with a modifying group for the cation represented by the formula (2).

According to the present invention, the contents of the graphite oxide and the biquaternary ammonium salt compound may vary within wide ranges; however, to give a better play to the synergetic effect between the graphite oxide and the biquaternary ammonium salt compound, preferably the weight ratio of the graphite oxide to the biquaternary ammonium salt compound is 1:30-300, more preferably is 1:40-280, even more preferably is 1:48-250, still more preferably is 1:90-200, and may be 1:180, for example.

According to the present invention, the graphite oxide can be prepared with a conventional method in the art. Preferably, the method for preparation of the graphite oxide comprises:

(a) subjecting graphite, potassium permanganate, and concentrated sulfuric acid to have a first oxidation reaction;

(b) subjecting the product of the first oxidation reaction to have a second oxidation reaction with hydrogen peroxide.

Wherein, in the step (a), the weight ratio of the graphite, the potassium permanganate and the concentrated sulfuric acid calculated by $H_2SO_4$ may be 100:250-300:400-450, for example. The graphite may be natural crystalline flake graphite that is available commercially. The concentration of the concentrated sulfuric acid may be 98 wt. % or higher, for example. Preferably, the conditions of the first oxidation reaction include: temperature of 40-60° C., time of 10-15 h. To control the first oxidation reaction in a better way, in the step (a), the graphite is mixed with the potassium permanganate before the first oxidation reaction is commenced, and then concentrated sulfuric acid is introduced to have the first oxidation reaction.

Wherein, in the step (b), preferably the weight ratio of the graphite to the hydrogen peroxide is 100:10-100. The hydrogen peroxide is provided in a form of water solution such as an aqueous hydrogen peroxide solution at 0.1-1 wt. % concentration may be used. The reaction temperature of the second oxidation reaction is −5° C. to 5° C., and the reaction process is quick, almost happens instantaneously, and the color of the suspension liquid changes from greyish green to golden yellow.

The graphite oxide can be obtained through the above-mentioned process. To extract the obtained graphite oxide, the process may further comprise: separating the product of the second oxidation reaction by solid-liquid separation (e.g., by filtering), washing the solid phase, and drying it (e.g., drying for 8-16 h at 80-100° C.).

According to the present invention, the contents of the graphite oxide and the biquaternary ammonium salt compound may vary within wide ranges; however, to give a better play to the synergetic effect between the graphite oxide and the biquaternary ammonium salt compound, preferably the weight ratio of the graphite oxide to the biquaternary ammonium salt compound is 1:30-300, more preferably is 1:40-280, even more preferably is 1:48-250, still more preferably is 1:90-200, and may be 1:180, for example.

The present invention further provides a method for preparation of a lubricant, which comprises:

in the presence of an acid, subjecting one or more of amine compounds represented by formula (3), one or more of epoxy compounds represented by formula (4) and graphite oxide to have a contact reaction in a solvent, wherein:

wherein each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; $R^3$ group is selected from H, C1-C20 alkyl, and C1-C20 hydroxyalkyl; X is halogen, preferably is Cl or Br.

According to the present invention, the groups in the compounds represented by formulae (3) and (4) may be selected as described above, and will not be detailed any more here.

Wherein, in a preferred embodiment of the present invention, the amine compound represented by the formula (3) is selected from one or more of N,N-dimethyl laurylamine, N,N-dimethyl tridecylamine, N,N-dimethyl tetradecylamine, N,N-dimethyl pentadecylamine, N,N-dimethyl hexadecylamine, N,N-dimethyl heptadecylamine, and N,N-dimethyl octadecylamine; the epoxy compound represented by formula (4) is epoxy chloropropane.

According to the present invention, the amine compound represented by formula (3) and the epoxy compound represented by formula (4) have a contact reaction with graphite oxide, so that the biquaternary ammonium salt compound described above is obtained through the reaction between the amine compound represented by formula (3) and the epoxy compound represented by formula (4); whereas, in the presence of graphite oxide, the graphite oxide may react with a part of the biquaternary ammonium salt compound to obtain graphite oxide that is partially linked with the modifying group provided by the biquaternary ammonium salt compound (see the groups shown in the above formula (2)); especially, the modifying group is linked to the outer edge of graphite oxide; more importantly, the biquaternary ammonium salt compound may be distributed between the layers of graphite oxide more easily, because the amine compound represented by formula (3) and the epoxy compound represented by formula (4), which are raw materials may be distributed between the layers of the graphite oxide in advance, so that reaction happens directly between the layers and thereby the biquaternary ammonium salt compound is obtained therein; thus, the biquaternary ammonium salt compound and the graphite oxide are dispersed more evenly. Thus, a nano-hybrid material is formed, and the obtained lubricant may be deemed as a nano-hybrid lubricant, which has outstanding lubricating property and heat-resistance property, and has lower impact on the rheological property of oil-based drilling fluid.

Wherein, the method for preparation of the graphite oxide has been described above, and will not be further detailed here; if applicable, the method for preparation of the lubricant may be deemed as including a preparation step of the graphite oxide.

According to the present invention, the dosage of the amine compound represented by formula (3) and the epoxy compound represented by formula (4) may vary within wide ranges; however, preferably, the molar ratio of the amine compound represented by formula (3) to the epoxy compound represented by formula (4) is 1.5-5:1, more preferably is 2-3:1.

Wherein, the dosage of the graphite oxide may vary within a wide range; however, to obtain a lubricant in which the graphite oxide and the biquaternary ammonium salt compound have a better synergistic effect between them, preferably, the weight ratio of the amount of the graphite oxide to the total amount of the amine compound represented by formula (3) and the epoxy compound represented by formula (4) is 1:30-350, more preferably is 1:40-310, even more preferably is 1:45-300, still more preferably is 1:65-280, and may be 1:100-250, for example.

According to the present invention, the acid not only can be used as a catalyst for catalyzing the contact reaction between the amine compound represented by formula (3) and the epoxy compound represented by formula (4), but also can provide anions to the obtained biquaternary ammonium salt compound. To that end, the acid may be selected properly according to the required anions. Preferably, the acid is one or more of hydrochloric acid, hydrobromic acid, and hydroiodic acid, and more preferably is hydrochloric acid. For example, hydrochloric acid at 35 wt. % or higher concentration, especially concentrated hydrochloric acid at 37 wt. % or higher concentration, may be used. There is no particular restriction on the dosage of the acid. For example, the molar ratio of the amine compound represented by formula (3) to the acid may be 0.5-4:1, and preferably is 1-3:1.

According to the present invention, the solvent may be any conventional solvent in the art; preferably, the solvent is one or more of methanol, ethanol, n-propanol, isopropanol, n-hexane, liquid paraffin, and methyl benzene. Wherein, there is no particular restriction on the amount of the solvent, as long as the amount of the solvent is enough to disperse the raw materials and promote the contact reaction. Preferably, the weight ratio of the graphite oxide to the solvent is 1:50-800, more preferably is 1:100-600, and even more preferably is 1:200-500.

According to the present invention, preferably, the conditions of the contact reaction include: temperature of 60-110° C. (preferably 80-100° C.) and time of 12-24 h (preferably 20-24 h). The above-mentioned substances are mixed (e.g., mixed by ultrasonic mixing for 30-100 min.) before the contact reaction is commenced, in order to make the reaction more complete and make the graphite oxide form a nanometer laminar structure.

According to the present invention, to extract the lubricant from the product of the contact reaction, the method may further comprise: removing the solvent from the product of the contact reaction (e.g., removing by reduced pressure distillation), and then drying, so as to obtain the lubricant.

The present invention further provides an oil-based drilling fluid containing the above mentioned lubricant.

According to the present invention, the oil-based drilling fluid that contains the lubricant in the present invention has greatly decreased lubrication coefficient, improved lubricating property, favorable rheological property and thermostability, and is suitable for use in operation at a high temperature. Preferably, based on 100 part by weight of oil phase in the drilling fluid, the content of the lubricant is 5 part by weight or less, alternatively is 0.5-2 part by weight, may be 1 part by weight for example.

According to the present invention, the oil phase in the drilling fluid may be any conventional oil phase in the art, such as one or more of diesel oil and white oil (e.g., white oil 3# (220° C. flash point, 3 mm$^2$/s kinematic viscosity at 40° C., and specific gravity=0.85), or white oil 5# (220° C. flash point, 3.5 mm$^2$/s kinematic viscosity at 40° C., and specific gravity=0.85). In addition, $CaCl_2$ water solution (preferably $CaCl_2$ water solution at 20-40 wt. % $CaCl_2$ concentration) in appropriate amount is added in the oil-based drilling fluid; for example, based on 100 part by weight of oil phase in the drilling fluid, the amount of the $CaCl_2$ water solution is 15-40 part by weight.

According to the present invention, the oil-based drilling fluid may further contain conventional additives used in oil-based drilling fluids; preferably, the oil-based drilling fluid contains one or more of emulsifier, a rheological modifier, wetting agent, filtrate reducer, alkalinity regulator, and weighting agent.

According to the present invention, advantageously the emulsifier is one or more of compounds represented by formula (I):

formula (I)

in the formula (I), each of the two $R_1$ groups is independently selected from C14-C30 alkyl optionally substituted by group Y and C14-C30 unsaturated alkyl with carbon-carbon double bonds optionally substituted by group Y, and the group Y is independently selected from the groups represented by the following formulae:

n is an integer in a range of 1-8; n X'-es are independently selected from H and —C(O)—$R_2$, and at least one X' is

—C(O)—R$_2$, R$_2$ is selected from carboxyl, C1-C6 alkyl, C3-C8 cycloalkyl, C1-C6 alkyl substituted by carboxyl, C3-C8 cycloalkyl substituted by carboxyl, C3-C8 cycloalkyl substituted by carboxyl and C1-C4 alkyl, C2-C6 unsaturated alkyl with a carbon-carbon double bond, C3-C8 unsaturated cycloalkyl with a carbon-carbon double bond, C2-C6 unsaturated alkyl with a carbon-carbon double bond substituted by carboxyl, and C3-C8 unsaturated cycloalkyl with a carbon-carbon double bond substituted by carboxyl and C1-C4 alkyl.

According to the present invention, the emulsifier is one or more of compounds represented by the formula (I). The compounds represented by formula represented by the formula (I) are compounds with a comb-like structure containing a long saturated and/or unsaturated alkyl chains at two ends and short alkyl chains in the middle. Through increasing membrane strength of emulsification interface and with the help of the the rheological modifier and the lubricant obtained in the present invention, such compounds with a comb-like structure can stabilize drilling fluid and make the drilling fluid have appropriate gel strength and density, thereby obtaining suspending power, and realizing the object of raising temperature resistance of drilling fluid under this case.

Wherein, preferably, in the formula (I), each of the two R$_1$ groups is independently selected from C14-C20 alkyl optionally substituted by group Y and C14-C20 unsaturated alkyl with a carbon-carbon double bond optionally substituted by group Y (preferably with not more than 5 carbon-carbon double bonds, 1, 2 or 3 for example); n is an integer of 1-6; R$_2$ is selected from carboxyl, C1-C4 alkyl, C4-C6 cycloalkyl, C1-C4 alkyl substituted by carboxyl, C4-C6 cycloalkyl substituted by carboxyl, C4-C6 cycloalkyl substituted by carboxyl and methyl, C2-C4 unsaturated alkyl with a carbon-carbon double bond (preferably with 1-3 carbon-carbon double bonds, 1, 2 or 3 for example), C4-C6 unsaturated cycloalkyl with a carbon-carbon double bond (preferably with not more than 5 carbon-carbon double bonds, 1, 2 or 3 for example), C2-C4 unsaturated alkyl with a carbon-carbon double bond substituted by carboxyl (preferably with 1-3 carbon-carbon double bonds, 1, 2 or 3 for example), and C4-C7 unsaturated cycloalkyl with a carbon-carbon double bond substituted by carboxyl and methyl (preferably with not more than 5 carbon-carbon double bonds, 1, 2 or 3 for example).

More preferably, in Formula (I), each of the two R$_1$ groups is independently selected from C15-C18 alkyl optionally substituted by group Y and C15-C18 unsaturated alkyl with a carbon-carbon double bond optionally substituted by group Y; n is an integer of 1-4, for example 1, 2, 3 or 4.

According to the present invention, each of the two R$_1$ groups can be selected respectively and independently, and the two R$_1$ groups may be the same or different from each other, wherein, examples of the R$_1$ group may include the following groups: —(CH$_2$)$_7$—CH═CH—(CH$_2$)$_7$—CH$_3$, —(CH$_2$)$_8$—CH(Y)—(CH$_2$)$_7$—CH$_3$, —(CH$_2$)$_7$—CH(Y)—(CH$_2$)$_8$—CH$_3$, —(CH$_2$)$_7$—CH(Y)—CH(Y)—(CH$_2$)$_7$—CH$_3$, —(CH$_2$)$_{16}$—CH$_3$, —(CH$_2$)$_7$—CH═CH—CH$_2$—CH═CH—(CH$_2$)$_4$—CH$_3$, —(CH$_2$)$_7$—CH═CH—CH$_2$—CH$_2$—CH(Y)—(CH$_2$)$_4$—CH$_3$, —(CH$_2$)$_7$—CH═CH—CH$_2$—CH(Y)—(CH$_2$)$_5$—CH$_3$, —(CH$_2$)$_8$—CH(Y)—CH$_2$—CH═CH—(CH$_2$)$_4$—CH$_3$, —(CH$_2$)$_7$—CH(Y)—CH$_2$—CH$_2$—CH═CH—(CH$_2$)$_4$—CH$_3$, —(CH$_2$)$_7$—CH═CH—CH$_2$—CH(Y)—CH(Y)—(CH$_2$)$_4$—CH$_3$, —(CH$_2$)$_7$—CH(Y)—CH(Y)—CH$_2$—CH═CH—(CH$_2$)$_4$—CH$_3$, —(CH$_2$)$_7$—CH(Y)—CH(Y)—CH$_2$—CH(Y)—(CH$_2$)$_5$—CH$_3$, —(CH$_2$)$_8$—CH(Y)—CH$_2$—CH(Y)—CH(Y)—(CH$_2$)$_4$—CH$_3$, —(CH$_2$)$_7$—CH(Y)—CH$_2$—CH$_2$—CH(Y)—CH(Y)—(CH$_2$)$_4$—CH$_3$, —(CH$_2$)$_7$—CH(Y)—CH(Y)—CH$_2$—CH$_2$—CH(Y)—CH(Y)—(CH$_2$)$_4$—CH$_3$, —(CH$_2$)$_7$—CH(Y)—CH(Y)—CH$_2$—CH(Y)—CH(Y)—(CH$_2$)$_4$—CH$_3$, —(CH$_2$)$_{14}$—CH$_3$, —(CH$_2$)$_{13}$—CH$_3$. where group Y, as described above, is selected from The connecting dotted lines on these groups stand for linkage sites linking the carbon atoms on R$_1$.

According to the present invention, examples of the group R$_2$ may include:

carboxyl, methyl, ethyl, propyl, cyclopentyl, cyclohexyl, —CH$_2$—COOH (referring to C1 alkyl substituted by a carboxyl group), —(CH$_2$)$_2$—COOH (referring to C2 alkyl substituted by a carboxyl group), —CH(CH$_2$—COOH)$_2$ (referring to C3 alkyl substituted by two carboxyl groups),

—CH$_2$—CH═CH$_2$,

—CH═CH$_2$—COOH, —CH$_2$—CH═CH$_2$—COOH, —CH═CH—CH$_2$—COOH,

According to the present invention, the foregoing emulsifier may be a product available in the market and may also be prepared by a conventional method of the art. Preferably, the method for preparing the emulsifier comprises: subjecting a polyamine compound represented by Formula (II) to take amidation reaction with one or more of carboxylic acids represented by Formula $R_{1'}$—COOH, and contacting and reacting the reaction product with one or more of carboxylic acids $R_2$—COOH and anhydrides thereof;

Formula (2)

where $R_2$ and n have been described above, so no necessary details will be given herein.

$R_{1'}$ is selected from C14-C30 alkyl and C14-C30 unsaturated alkyl with a carbon-carbon double bond.

Wherein, examples of the carboxylic acid represented by formula $R_{1'}$—COOH may include: COOH—$(CH_2)_7$—CH=CH—$(CH_2)_7$—$CH_3$ (also referred to as oleic acid), COOH—$(CH_2)_7$—CH=CH—$CH_2$—CH=CH—$(CH_2)_4$—$CH_3$ (also referred to as linoleic acid), COOH—$(CH_2)_{16}$—$CH_3$ (also referred to as octadecanoic acid), COOH—$(CH_2)_{14}$—$CH_3$ (also referred to as hexadecanoic acid or palmitic acid), and COOH—$(CH_2)_{13}$—$CH_3$ (also referred to as pentadecanoic acid).

Wherein, examples of the carboxylic acid represented by the formula $R_2$—COOH and its anhydride may include: HOOC—COOH (oxalic acid), $CH_3$—COOH (acetic acid), $CH_3$—COO—CO—$CH_3$ (acetic anhydride), HOOC—$CH_2$—COOH (propandioic acid), HOOC—$CH_2$—$CH_2$—COOH (butanedioic acid), HOOC—$CH_2$—CH(COOH)—$CH_2$—COOH (tricarballylic acid), (succinic anhydride),

(1,2-adipic acid), (1,2-adipic anhydride), maleic acid, (maleic anhydride),

(methyl nadic anhydride), (nadic anhydride).

According to the present invention, the embodiments of the polyamine represented by Formula (II) for example may include:

(called as diethylenetriamine)

(called as triethylenetetramine)

(called as tetraethylenepentamine)

(called as pentaethylenehexamine)

According to the present invention, the amidation reaction between the polyamine represented by foregoing Formula (II) and the carboxylic acid represented by $R_{1'}$—COOH mainly refers to the amidation reaction between the primary amine of the polyamine represented by foregoing Formula (II) and the carboxylic group of the carboxylic acid represented by $R_{1'}$—COOH, with water molecules removed to form amido bonds, thereby obtaining one or more of compounds with secondary amine not substituted in the middle of the chain as represented by Formula (I')

Preferably, the molar ratio of the polyamine compound represented by Formula (II) and the carboxylic acid represented by Formula $R_{1'}$—COOH is 1:1.8 to 1:3, preferably 1:1.8 to 1:2.2.

According to the present invention, preferably, the conditions of the amidation reaction comprise: the temperature is a temperature of 220-230° C., pH value of 7-9 and a time of 3-5 h. In order to make amidation reaction more sufficient, this method may further comprise: firstly mixing the polyamine represented by Formula (II) with one or more of carboxylic acids represented by $R^{1'}$—COOH for 10-30 min under a stirring rate of 80-300 r/min, then taking the amidation reaction under a stirring rate of 80-300 r/min, and water is trapped by water knockout trap during amidation reaction.

According to the present invention, the emulsifier of the present invention may be obtained through contacting and reacting the above reaction product of the amidation reaction with one or more of the carboxylic acids represented by $R_2$—COOH and anhydrides thereof. The reaction product of amidation reaction may be purified to obtain the compound represented by alternatively, the reaction product of amidation reaction without purification may directly contact and react with one or more of the carboxylic acids represented by $R_2$—COOH and anhydrides thereof so as to link —C(O)—$R_2$ substituent to the secondary amine between two amido bonds, thereby forming the compound with a comb-like structure represented by Formula (I). Preferably, the molar ratio of the polyamine compound represented by Formula (II) and the carboxylic acids represented by Formula $R_2$—COOH and anhydrides thereof is 1:0.5 to 1:20. For example, the molar ratio of the polyamine compound represented by Formula (II) and the carboxylic acids represented by Formula $R_2$—COOH and anhydrides thereof is 1:1.8 to 1:2.2, 1:3.6 to 1:4.4, 1:5.4 to 1:6.6, 1:7.2 to 1:8.8, 1:9 to 1:11, 1:10.8 to 1:13.2.

According to the present invention, when the carboxylic acid represented by $R_1$—COOH is an unsaturated carboxylic acid with a carbon-carbon double bond, and the carboxylic acids represented by Formula $R_2$—COOH and anhydrides thereof adopted in the process of the contract reaction also contain a carbon-carbon double bond, then in the process of the contact reaction, addition reaction may also occur between the carbon-carbon double bond in the carboxylic acids represented by Formula $R_2$—COOH (and anhydrides thereof) and the carbon-carbon double bond in the reaction product of the amidation reaction, thereby obtaining the compound with $R_1$ (shown in Formula (I)) substituted by group Y. Although the present invention does not have particular limitation to this, the compound obtained under this case is also included in the emulsifier described in the present invention.

According to the present invention, preferably, the conditions of the contact reaction comprise: a temperature of 75-90° C., pH value of 7-9 and a time of 6-10 h. In order to make contact reaction more sufficient, this method may further comprise: contacting and reacting the reaction product of the amidation reaction with one or more of the carboxylic acids represented by Formula $R_2$—COOH and anhydrides thereof under a stirring rater of 200-500 r/min, and water is trapped by water knockout trap during the contact reaction.

According to the present invention, it should be noted that the emulsifier of the present invention may be one of the compounds represented by Formula (I), but if the foregoing preparation method is adopted, the emulsifier may also be one of the compounds represented by Formula (I) obtained through purifying and separating the product obtained by the foregoing preparation method. However, as more effective operation, the emulsifier of the present invention may be more of the compounds represented by Formula (I), i.e.: if the foregoing preparation method is adopted, the emulsifier may be a product directly obtained by the foregoing preparation method and is uses without purification. In other words, it may be understood that the emulsifier of the present invention is a product obtained by the foregoing method without purification.

More preferably, based on 100 part by weight of oil phase in the drilling fluid, the amount of the emulsifier is 1-5 part by weight.

According to the present invention, the rheological modifier preferably is a dimer acid-organic amine copolymer comprising structural units from dimer acid, structural units from alkylamine, and structural units from arylamine, wherein, the dimer acid is a dimer of oleic acid and linoleic acid, the alkylamine is one or more of C10-C20 alkyl primary amines, the arylamine is aniline and aniline substituted by C1-C3 alkyl at one or more sites on benzene ring. More preferably, the rheological modifier is the dimer acid-organic amine copolymer. Wherein, the dimer acid is a dimer fatty acid containing two carboxyl groups, which is a dimer of oleic acid ($CH_3(CH_2)_7CH$=$CH(CH_2)_7COOH$) and linoleic acid ($CH_3(CH_2)_4CH$=$CHCH_2CH$=$CH(CH_2)_7COOH$). Such a dimer acid may be obtained with a conventional method according to the present invention, such as the method described in the article "Shulin Zhang, Synthesis and Application of Dimer Acid, *Fine Petrochemical Industry*, 1995", or may be a commercial product (preferably the purity is 98 wt. % or higher). Preferably, the alkylamine is one or more of dodecyl primary amine, tridecyl primary amine, tetradecyl primary amine, pentadecyl primary amine, hexadecyl primary amine, heptadecyl primary amine, and octodecyl primary amine, more preferably is dodecyl primary amine and/or octodecyl primary amine. Preferably, the arylamine is one or more of aniline, 2-methylaniline, 3-methylaniline, 4-methylaniline, 2-ethylaniline, 3-ethylaniline, 4-ethylaniline, 2-propylaniline, 3-propylaniline, and 4-propylaniline, and more preferably is one or more of aniline, 2-methylaniline, 3-methylaniline, and 4-methylaniline.

In a preferred embodiment of the present invention, the dimer acid is a dimer of oleic acid and linoleic acid, the alkylamine is dodecyl primary amine or octodecyl primary amine, and the arylamine is aniline or 3-methylaniline.

According to the present invention, preferably, the molar ratio of the structural units from dimer acid to the structural units from alkylamine to the structural units from the dimer acid, structural units from the alkylamine and structural units from the arylamine is 1:0.3-1:0.2-1, more preferably 1:0.3-0.8:0.2-0.7, further more preferably 1:0.4-0.7:0.3-0.6.

Preferably, the weight-average molecular weight of the dimer acid-organic amine copolymer is 2,200-9,000 g/mol, and the absolute viscosity thereof is 20,000-150,000 cp p. Considering from the perspective of obtaining a composition more suitable for raising suspending power and temperature resistance of clay-free whole-oil-based drilling fluid, more preferably, the weight-average molecular weight of the dimer acid-organic amine copolymer is 4,000-9,000 g/mol, and the absolute viscosity thereof is 100,000-150,000 cp. More preferably, the weight-average molecular weight of the dimer acid-organic amine copolymer is 5,000-9,000 g/mol, and the absolute viscosity thereof is 100,000-150,000 cp. In the present invention, weight-average molecular weight is measured by GPC (gel permeation chromatography), and absolute viscosity is measured by Brookfield viscometer.

According to the present invention, the dimer acid-organic amine copolymer as rheological modifier may be prepared by a conventional method of the ar. For example, the method for preparing the dimer acid-organic amine copolymer comprises: copolymerizing the dimer acid, the alkylamine and the arylamine. In this method, the dimer acid, alkylamine and arylamine have been described above, so no necessary details will be given herein.

According to the present invention, the foregoing copolymerization reaction among dimer acid, alkylamine and arylamine is mostly dehydration condensation reaction between carboxylic acids and amines. By copolymerization reaction among dimer acid, alkylamine and arylamine in the present invention alone, a dimer acid-organic amine copolymer with good performance may be obtained as a rheological modifier of whole-oil-based drilling fluid, but in order to obtain a rheological modifier with absolute viscosity and molecular weight more suitable for whole-oil-based drilling fluid, the molar ratio of the dimer acid, alkylamine and arylamine is preferably 1:0.3-1:0.2-1, more preferably 1:0.3-0.8:0.2-0.7, further more preferably 1:0.4-0.7:0.3-0.6.

According to the present invention, the copolymerization reaction may adopt a conventional method of the art as long as a dimer acid-organic amine copolymer that may be used as a rheological modifier of the composition can be obtained. Preferably, before copolymerization of dimer acid, alkylamine and arylamine, they are mixed to obtain a monomer mixture; then with the existence of concentrated sulfuric acid, the obtained monomer mixture takes copolymerization reaction.

According to the present invention, if the dimer acid, alkylamine and arylamine are mixed at first to obtain monomer mixture, the monomers can more sufficiently contact each other in the subsequent polymerization reaction. As the foregoing monomer mixture is sticky, preferably the mixing is conducted at higher temperature, and particularly preferably the adopted mixing conditions include: a temperature of 100-130° C. and a time of 20-30 min.

According to the present invention, when the foregoing concentrated sulfuric acid is used as a catalyst of the copolymerization reaction in the present invention, there is no particular limitation to its dose as long as it can catalyze the copolymerization reaction in the present invention. Preferably, based on the total weight of the dimer acid, alkylamine and arylamine, the dose of the concentrated sulfuric acid is 0.3-1 wt. %. The concentrated sulfuric acid may be a sulfuric acid solution with sulfuric acid concentration of 95 wt. % or above (preferably 98 wt. %).

According to the present invention, preferably, the conditions of the copolymerization reaction comprise: a temperature of 150-180° C. and a time of 2-6 h. More preferably, the conditions of the copolymerization reaction comprise: a temperature of 155-175° C. and a time of 2-6 h. Further more preferably, the conditions of the copolymerization reaction comprise: a temperature of 160-170° C. and a time of 2-6 h.

In order to promote the copolymerization reaction, byproduct water of copolymerization reaction may be removed from the reaction system. The method for removing byproduct water is a conventional method of the art, so no necessary details will be given here.

When the foregoing method is adopted to prepare dimer acid-organic amine copolymer, the rheological modifier may be either the dimer acid-organic amine copolymer prepared by the foregoing method, or a 50-70 wt. % solution obtained by directly using a diluent to dilute the dimer acid-organic amine copolymer prepared by the foregoing method (in other words, based on the total weight of the dimer acid-organic amine copolymer solution after dilution, the content of dimer acid-organic amine copolymer is 50-70 wt. %), or a rheological modifier of the present invention obtained by other methods well known in the art and containing the dimer acid-organic amine copolymer.

Those skilled in the art should understand that the product of copolymerization reaction is not separated in general and it is believed that all the adopted monomers basically take complete reaction and the product of copolymerization reaction is directly used as copolymer. Therefore, for the sake of convenience, the diluent may be directly added to the products of the copolymerization reaction after the copolymerization reaction in the method for preparing the foregoing dimer acid-organic amine copolymer is completed, and there is no need to purify and separate the dimer acid-organic amine copolymer in it. In a general sense, the dimer acid-organic amine copolymer referred to in the present invention is also the product of the copolymerization reaction without purification and separation, or the product of copolymerization reaction obtained after only byproduct water is removed as described above.

The diluent for example may be a diluent conventionally adopted in the art, such as: tall oil and/or tall oil fatty acid.

Preferably, based on 100 part by weight of oil phase in the drilling fluid, the amount of the rheological modifier is 1-5 part by weight.

Wherein, the wetting agent can improve the wetting property of drilling fluid, and prevent complex downhole conditions, such as jamming of drilling tool, etc.; for example, the wetting agent may be one or more of modified phospholipid (e.g., FHGT-G modified phospholipid from Shanghai Youchuang Industrial Co., Ltd.) and a mixture of fatty glyceride and surfactant (e.g., FK-1), and preferably is FHGT-G modified phospholipid. More preferably, based on 100 part by weight of oil phase in the drilling fluid, the amount of the lubricant is 0.5-2 part by weight.

Wherein, the filtrate reducer can improve the fluid loss control and wall-building properties of drilling fluid; for example, the filtrate reducer may be one or more of oxidized asphalt, modified humic acid, and polymeric oil-based filtrate reducer (e.g., sulphonated polystyrene), and preferably is modified humic acid and/or polymeric oil-based filtrate reducer. Preferably, based on 100 part by weight of oil phase in the drilling fluid, the amount of the filtrate reducer is 1-3 part by weight.

Wherein, the alkalinity regulator has effects of stabilizing the emulsion and improving emulsion-breaking voltage; for example, the alkalinity regulator may be CaO. Preferably, based on 100 part by weight of oil phase in the drilling fluid, the amount of the alkalinity regulator is 2-5 part by weight.

Wherein, the weighting agent has an effect of adjusting the density of drilling fluid to desired density; for example, the weighting agent may be barite (e.g., barite with 90 wt. % or higher barium sulfate content), etc. Preferably, based on 100 part by weight of oil phase in the drilling fluid, the amount of the weighting agent is 400-500 part by weight.

The above-mentioned additives may be commercial products, or may be prepared with conventional methods in the art. They will not be further detailed here.

According to the present invention, by adding the composition obtained in the present invention, the obtained oil-based drilling fluid with 2.6 g/cm$^3$ density may have a greatly decreased lubrication coefficient after hot aging at 200° C.; preferably the lubrication coefficient is decreased by 40% or more, particularly preferably decreased by 55% or more, more preferably decreased by 60% or more; in addition, the drilling fluid maintains favorable rheological property and has high thermostability, and is suitable for use in operation at a high temperature.

The present invention further provides an application of the oil-based drilling fluid in oil and gas drilling.

Hereunder the present invention will be detailed in embodiments.

In the following examples and comparative examples:

The infrared spectrums are measured with a MAGNA-IR 560 Fourier transform infrared spectrometer from SpectraLab Scientific.

The $^1$H-NMR spectrums and $^{13}$C-NMR spectrums are measured with an AVANCE 400 NMR spectrometer from Bruker.

The SEM spectrums are measured with a SU-8010 SEM analyzer from Hitachi.

The TEM spectrums are measured with a JEM-2100 TEM analyzer from JEOL.

Graphite Oxide Preparation Example 1

Figure 1:
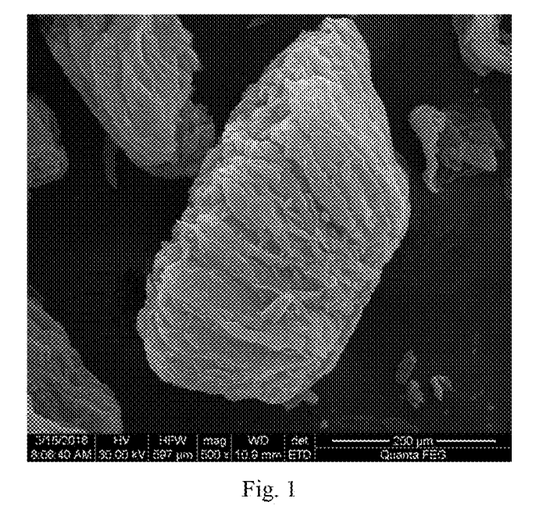
FIG. 1 shows a 500×SEM image of the graphite oxide obtained in a preparation example in the present invention.
Figure 2:
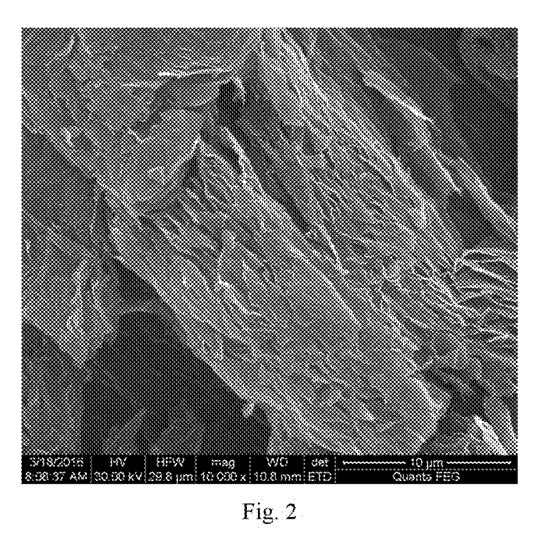
FIG. 2 shows a 10,000×SEM image of the graphite oxide obtained in a preparation example in the present invention.

423 g concentrated sulfuric acid (at 98 wt. % concentration) is added into a mixture of 10 g graphite (325 mesh natural crystalline flake graphite from Qingdao Santong Graphite Co., Ltd.) and 30 g potassium permanganate at room temperature (approx. 25° C.), and then the materials are stirred and heated up to 50° C., and held at the temperature for reaction for 12 h while stirring; the reaction product is cooled to room temperature (approx. 25° C.), poured into 400 g of 0.4 wt. % aqueous hydrogen peroxide solution (ice water solution, at 0° C. temperature); now the mixed solution changes from greyish green color to golden yellow color. The product is filtered and washed, till the filtrate is neutral, then the product is dried at 100° C. for about 10 h; thus, 10 g graphite oxide is obtained, a 500×SEM image of the graphite oxide is shown in FIG. 1, and a 10,000×SEM image is shown in FIG. 2.

Emulsifier Preparation Example 1

(1) The reactants are mixed at a molar ratio of tetraethylene pentamine to linoleic acid=1:2.2 (i.e., the molar ratio of tetraethylene pentamine calculated by primary amine group to linoleic acid is 1:1.1), and stirred for 40 min at 250 r/min stirring rate, then the pH of the obtained mixture is adjusted to 9, and the mixture is kept at 230° C. for reaction for 3 h, while water is separated with a water separator in the process, next, the product is cooled to room temperature;

(2) The reaction product in the step (1) is mixed with propandioic acid (the molar ratio of the tetraethylene pentamine to the propandioic acid is 1:0.6), then the pH of the obtained mixture is adjusted to 8, next, the mixture is stirred at 400 r/min. at 90° C. for reaction for 6 h; thus, an emulsifier A1 is obtained. Detected and analyzed by infrared spectroscopy, $^1$H-NMR spectroscopy, and $^{13}$C-NMR spectroscopy, the emulsifier A1 contains amido groups, unsaturated double bonds, and carboxyl groups, and is in a comb structure.

Rheological Modifier Preparation Example 1

(1) Dimer acid (Pripol 1013 from Shanghai Heribit Chemical Co., Ltd., the same below), dodecyl primary amine, and aniline are added at 1:0.5:0.5 molar ratio into a reaction vessel, and the materials are stirred at 120±2° C. for 30 min.; thus, a homogeneous mixture of monomers is obtained;

(2) Concentrated sulfuric acid (at 98 wt. % concentration, the added amount is 0.5 wt. % of the weight of the mixture of monomers) is added by dropwise into the mixture of monomers (within about 2 min.), with a condensate drain device deployed, the mixture is kept at 160±5° C. for reaction for 2 h; the obtained reaction product is dimer acid-organic amine copolymer, which has 6,500 g/mol weight-average molecular weight and 125,000 cp absolute viscosity.

Tall oil diluent (tall oil F1 from Jinan Jinquan Chemical Co., Ltd, the same below) is added into the dimer acid-organic amine copolymer, to dilute the dimer acid-organic amine copolymer to 50 wt. % concentration; thus, a rheological modifier B1 described in the present invention is obtained, and the rheological modifier liquid is orange liquid.

Example 1

This example is used to describe the lubricant and its preparation method of the present invention.

17.1 g (80 mmol) N,N-dimethyl lauryl amine, 4 g concentrated hydrochloric acid (at 37 wt. % concentration), 3.4 g (36.4 mmol) epoxy chloropropane, and 0.1 g graphite oxide are added into 50 g ethanol, and the materials are mixed by ultrasonic mixing for 1 h; then, the homogeneous solution is kept at 80° C. for reaction for 24 h in reflux mode; next, the solvent is removed by reduced pressure distillation, and the product is cooled and dried; thus, 18 g lubricant L1 is obtained, in which the weight ratio of graphite oxide to biquaternary ammonium salt compound is 1:180.

Figure 3:
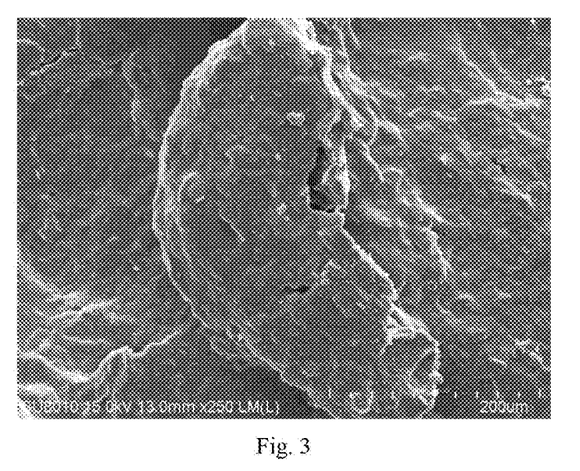
FIG. 3 is a 250×SEM image of the lubricant obtained in example 1 of the present invention.
Figure 4:
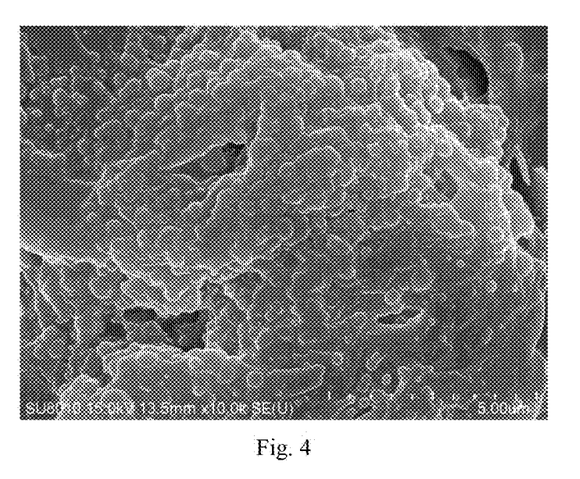
FIG. 4 is a 10,000×SEM image of the lubricant obtained in example 1 of the present invention.

Analyzed by infrared spectrometry, NMR spectrometry, and mass spectrometry, the lubricant L1 contains a biquaternary ammonium salt compound represented by the formula (1-1-1), which is chemically linked with graphite oxide as modifying group represented by the formula (2) ($R^1$ is H, $R^2$ is methyl, and $R^3$ is n-butyl); analyzed by SEM and TEM, in the lubricant L1, the biquaternary ammonium salt compound adheres to the graphite oxide on the surface and between the layers, wherein, a 250×SEM image is shown in FIG. 3, and a 10,000×SEM image is shown in FIG. 4.

Example 2

This example is used to describe the lubricant and its preparation method of the present invention.

According to the method described in the example 1, the difference is that 19.3 g (80 mmol) N,N-dimethyl tetradecylamine is used to replace the N,N-dimethyl laurylamine, the product is cooled and dried, and thus 20 g lubricant L2 is obtained, wherein, the weight ratio of the graphite oxide to the biquaternary ammonium salt compound is 1:200.

Analyzed by infrared spectrometry, NMR spectrometry, and mass spectrometry, the lubricant L2 contains a biquaternary ammonium salt compound represented by the formula (1-3-1), which is chemically linked with the graphite oxide as modifying group represented by the formula (2) ($R^1$ is H, $R^2$ is methyl, and $R^3$ is n-hexyl); analyzed by SEM and TEM, in the lubricant L2, the biquaternary ammonium salt compound adheres to the graphite oxide on the surface and between layers.

Example 3

This example is used to describe the lubricant and its preparation method of the present invention.

According to the method described in the example 1, the difference is that 21.6 g (80 mmol) N,N-dimethyl hexadecylamine is used to replace the N,N-dimethyl laurylamine, the product is cooled and dried, and thus 23 g lubricant L3 is obtained, wherein, the weight ratio of the graphite oxide to the biquaternary ammonium salt compound is 1:220.

Analyzed by infrared spectrometry, NMR spectrometry, and mass spectrometry, the lubricant L3 contains a biquaternary ammonium salt compound represented by the formula (1-5-1), which is chemically linked with the graphite oxide as modifying group represented by the formula (2) ($R^1$ is H, $R^2$ is methyl, and $R^3$ is n-octyl); analyzed by SEM and TEM, in the lubricant L3, the biquaternary ammonium salt compound adheres to the graphite oxide on the surface and between layers.

Example 4

This example is used to describe the lubricant and its preparation method of the present invention.

According to the method described in the example 1, the difference is that 23.8 g (80 mmol) N,N-dimethyl octadecylamine is used to replace the N,N-dimethyl laurylamine, the product is cooled and dried, and thus 24 g lubricant L4-1 is obtained, wherein, the weight ratio of the graphite oxide to the biquaternary ammonium salt compound is 1:240.

Analyzed by infrared spectrometry, NMR spectrometry, and mass spectrometry, the lubricant L4-1 contains a biquaternary ammonium salt compound represented by the formula (1-7-1), which is chemically linked with the graphite oxide as modifying group represented by the formula (2) ($R^1$ is H, $R^2$ is methyl, and $R^3$ is n-decyl); analyzed by SEM and TEM, in the lubricant L4-1, the biquaternary ammonium salt compound adheres to the graphite oxide on the surface and between layers.

Example 5

This example is used to describe the lubricant and its preparation method of the present invention.

23.8 g (80 mmol) N,N-dimethyl octadecylamine, 5.4 g concentrated hydrochloric acid (at 37 wt. % concentration), 2.5 g (26.7 mmol) epoxy chloropropane, and 0.2 g graphite oxide are added into 50 g ethanol, and the materials are mixed by ultrasonic mixing for 40 min.; then, the homogeneous solution is kept at 85° C. for reaction for 22 h in reflux mode; next, the solvent is removed by reduced pressure distillation, and the product is cooled and dried; thus, 18 g lubricant L4-2 is obtained, in which the weight ratio of graphite oxide to biquaternary ammonium salt compound is 1:90.

Analyzed by infrared spectrometry, NMR spectrometry, and mass spectrometry, the lubricant L4-2 contains a biquaternary ammonium salt compound represented by the formula (1-7-1), which is chemically linked with the graphite oxide as modifying group represented by the formula (2) ($R^1$ is H, $R^2$ is methyl, and $R^3$ is n-decyl); analyzed by SEM and TEM, in the lubricant L4-2, the biquaternary ammonium salt compound adheres to the graphite oxide on the surface and between layers.

Example 6

This example is used to describe the lubricant and its preparation method of the present invention.

23.8 g (80 mmol) N,N-dimethyl octadecylamine, 2.7 g concentrated hydrochloric acid (at 37 wt. % concentration), 3.7 g (40 mmol) epoxy chloropropane, and 0.4 g graphite oxide are added into 80 g ethanol, and the materials are mixed by ultrasonic mixing for 40 min.; then, the homogeneous solution is kept at 90° C. for reaction for 20 h in reflux mode; next, the solvent is removed by reduced pressure distillation, and the product is cooled and dried; thus, 24 g lubricant L4-3 is obtained, in which the weight ratio of graphite oxide to biquaternary ammonium salt compound is 1:60.

Analyzed by infrared spectrometry, NMR spectrometry, and mass spectrometry, the lubricant L4-3 contains a biquaternary ammonium salt compound represented by the formula (1-7-1), which is chemically linked with the graphite oxide as modifying group represented by the formula (2) ($R^1$ is H, $R^2$ is methyl, and $R^3$ is n-decyl); analyzed by SEM and TEM, in the lubricant L4-3, the biquaternary ammonium salt compound adheres to the graphite oxide on the surface and between layers.

Example 7

This example is used to describe the lubricant and its preparation method of the present invention.

According to the method described in the example 4, the difference is that the amount of N,N-dimethyl octadecylamine is 26.8 g (90 mmol), and the epoxy chloropropane is 3.8 g (41 mmol); thus, 28 g lubricant L4-4 is obtained, wherein, the weight ratio of the graphite oxide to the biquaternary ammonium salt compound is 1:280.

Example 8

This example is used to describe the lubricant and its preparation method of the present invention.

According to the method described in the example 4, the difference is that 0.6 g graphite oxide is used; thus, 24 g lubricant L4-4 is obtained, wherein, the weight ratio of the graphite oxide to the biquaternary ammonium salt compound is 1:40.

Drilling Fluid Example 1

This example is provided to describe the drilling fluid in the present invention.

The formation is: 100 part by weight of diesel oil (diesel oil 0# from Beijing Jinbaoli, the same below), 20 part by weight of $CaCl_2$ water solution (the $CaCl_2$ concentration in the solution is 30 wt. %), 1 part by weight of lubricant L1, 3 part by weight of emulsifier A1, 2 part by weight of rheological modifier B1, 1 part by weight of modified phospholipid wetting agent (e.g., FHGT-G modified phospholipid from Shanghai Youchuang Industrial Co., Ltd., the same below), 2 part by weight of polymeric oil-based filtrate reducer (HFLO oil-based filtrate reducer from Sichuan Honghua), 3 part by weight of CaO, 450 part by weight of barite (from Sichuan Zhengrong, the same below); thus, a drilling fluid X1 is prepared, and the density of it is 2.6 g/cm³.

Drilling Fluid Examples 2-8

These examples are provided to describe the composition and the drilling fluid in the present invention.

According to the formation used in the drilling fluid example 1, the difference is that the lubricant L2-L3 and L4-1 to L4-4 are used respectively to replace the lubricant L1; thus, drilling fluids X2-X8 are obtained, and the density is 2.6 g/cm³.

Comparative Example 1

According to the formation used in the drilling fluid example 1, the difference is that the lubricant L1 is not added; thus, a drilling fluid DX1 is prepared.

Comparative Example 2

According to the formation used in the drilling fluid example 1, the difference is that the graphite oxide obtained in the preparation example 1 is used to replace the lubricant L1; thus, a drilling fluid DX2 is prepared.

Comparative Example 3

According to the formation used in the drilling fluid example 1, the difference is that an EZ-MUL emulsifier from Halliburton is used to replace the emulsifier A1; thus, a drilling fluid DX3 is prepared.

Test Example

The drilling fluids X1-X8 and DX1-DX2 are tested at room temperature without hot aging and after hot aging at 200° C. for 16 h respectively, to test their plastic viscosity (PV), apparent viscosity (AV), yield point (YP), emulsion-breaking voltage and lubrication coefficient (K), and calculate reduced rate ($R_k$) of lubrication coefficient. The results are shown in Table 1, wherein:

The plastic viscosity (PV) is measured with a FANN six-speed viscosity meter with the method specified in the national standard GB/T29170-2012, in unit of mPa·s, $PV=\theta_{600}-\theta_{300}$.

The apparent viscosity (AV) is measured with a FANN six-speed viscosity meter with the method specified in the national standard GB/T29170-2012, in unit of mPa·s, $AV=\frac{1}{2}\theta_{600}$.

The yield point (YP) is measured with a FANN six-speed viscosity meter with the method specified in the national standard GB/T29170-2012 $YP=0.5(2\theta_{300}-\theta_{600})$, in unit of Pa.

The lubrication coefficient K refers to the ratio of the friction force between two friction surfaces to the normal load, and is measured with an E-P extreme pressure lubricity tester with the method specified in the petroleum industry standard SY/T6094-1994.

The reduced rate $R_k$ of lubrication coefficient refers to the reduced rate of lubrication coefficient of a drilling fluid after lubricant is added in relation to the lubrication coefficient of the drilling fluid without lubricant. The calculation formula is:

$$R_k=[(K_0-K)/K_0]\times 100\%,$$

wherein, $R_k$ means reduced rate of lubrication coefficient, %; $K_0$ means lubrication coefficient of the drilling fluid without lubricant (i.e., the lubrication coefficient of the drilling fluid DX1); K means the lubrication coefficient of the drilling fluid after a nano-hybrid lubricant is added.

The emulsion-breaking voltage is measured with an electrical stability tester (Model D90-300 from Qingdao Jiaonan Analytical Instrument Factory, the same below), and it refers to the voltage when water-in-oil mud begins to break, and reflects the electrical stability of the water-in-oil mud. A higher emulsion-breaking voltage indicates that the mud can maintain in emulsion state in a wider range and has higher stability; a lower emulsion-breaking voltage indicates the mud has lower stability. In the testing process, electrodes are inserted into the emulsion mud to be tested, an applicable step voltage multiplier is selected, and the voltage across the electrodes is increased gradually, till the electrical stability tester indicates that the emulsion mud has broken; then, the voltage reading when the emulsion mud begins to break is logged.

TABLE 1

| Drilling Fluid | Condition | AV mPa·s | PV mPa·s | YP Pa | K | $R_k$% |
|---|---|---|---|---|---|---|
| X1 | Before hot aging | 84 | 76 | 8 | 0.102 | 42.7% |
|    | After hot aging  | 80 | 71 | 9 | 0.111 | 41.9% |
| X2 | Before hot aging | 88 | 79 | 9 | 0.090 | 49.4% |
|    | After hot aging  | 82 | 72 | 10 | 0.096 | 49.7% |
| X3 | Before hot aging | 95 | 84 | 11 | 0.074 | 58.4% |
|    | After hot aging  | 85 | 75 | 10 | 0.082 | 57.1% |
| X4 | Before hot aging | 106 | 99 | 7 | 0.068 | 61.8% |
|    | After hot aging  | 96 | 90 | 6 | 0.073 | 61.8% |
| X5 | Before hot aging | 104 | 96 | 8 | 0.076 | 57.3% |
|    | After hot aging  | 92 | 84 | 8 | 0.079 | 58.6% |
| X6 | Before hot aging | 98 | 89 | 9 | 0.081 | 54.5% |
|    | After hot aging  | 90 | 81 | 9 | 0.085 | 55.5% |
| X7 | Before hot aging | 96 | 88 | 8 | 0.111 | 37.6% |
|    | After hot aging  | 92 | 83 | 9 | 0.123 | 35.6% |
| X8 | Before hot aging | 108 | 98 | 10 | 0.119 | 35.1% |
|    | After hot aging  | 104 | 93 | 11 | 0.128 | 33.9% |
| DX1 | Before hot aging | 100 | 92 | 8 | 0.178 | / |
|     | After hot aging  | 87 | 80 | 7 | 0.191 | / |
| DX2 | Before hot aging | 102 | 93 | 9 | 0.121 | 32.0% |
|     | After hot aging  | 92 | 81 | 11 | 0.132 | 30.1% |

Note:
"/" represents without data.

It is seen from the data in Table 1: the lubricant provided in the present invention can effectively improve the lubricating property of the obtained drilling fluid; thus, the lubrication coefficient of the obtained drilling fluid is greatly decreased, preferably the reduced rate of the lubrication coefficient is 40% or higher, particularly preferably is 55% or higher, more preferably is 60% or higher. Especially, the above-mentioned lubricating effect varies little before and after hot aging at 200° C., indicating that the lubricant provided in the present invention has a favorable temperature resistance property, and is suitable for use in operation at a high temperature. Furthermore, compared with the drilling fluid DX1 (blank sample), the rheological property (i.e., plastic viscosity (PV), apparent viscosity (AV), and yield point (YP)) of the drilling fluid in the present invention before and after hot aging have no significant difference, which indicates the lubricant provided in the present invention maintains a good rheological property.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the protected scope of the present invention.

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:
1. A lubricant comprising:
   a) graphite oxide; and
   b) a biquaternary ammonium salt compound, wherein the cation of the biquaternary ammonium salt compound is represented by formula (1);
wherein the biquaternary ammonium salt compound adheres to the surface of the graphite oxide and optionally adheres to the graphite oxide between layers of the graphite oxide; and part of the biquaternary ammonium salt compound is linked to the graphite oxide in the form of a modifying group, wherein the cation of the modifying group is represented by formula (2):

wherein each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; and each $R^3$ group is independently selected from n-hexyl, n-heptyl, n-octyl, n-nonyl, n-decyl, undecyl, and dodecyl,
wherein a weight ratio of the graphite oxide to the biquaternary ammonium salt compound is 1: 48-250.

2. The lubricant according to claim 1, wherein each $R^1$ group is independently selected from H, hydroxyl, halogen, C1-C4 alkyl, C1-C4 alkoxy, and C1-C4 hydroxyalkyl; each $R^2$ group is independently selected from H and C1-C4 alkyl.

3. The lubricant according to claim 2, wherein each $R^1$ group is independently selected from H, hydroxyl, methyl, ethyl, methoxy, ethoxy, hydroxymethyl, and hydroxyethyl; each $R^2$ group is independently selected from H, methyl, ethyl, n-propyl, and n-butyl.

4. The lubricant according to claim 3, wherein each $R^1$ group is independently selected from H, methyl, and ethyl; each $R^2$ group is independently selected from H, methyl, ethyl, n-propyl, and n-butyl; and each $R^3$ group is independently selected from n-hexyl, n-heptyl, n-octyl, n-nonyl, and n-decyl.

5. The lubricant according to claim 2, wherein the cation of the biquaternary ammonium salt compound is selected from one or more of the following:

6. The lubricant according to claim 1, wherein the anion of the biquaternary ammonium salt compound is selected from one or more of Cl$^-$, Br$^-$, and I$^-$.

7. A method for preparing a lubricant according to claim 1, the method comprising:
   reacting one or more amine compounds represented by formula (3), one or more epoxy compounds represented by formula (4), and graphite oxide, wherein the reaction is carried out in a solvent and in the presence of an acid, wherein:

and
   wherein each $R^1$ group is independently selected from H, hydroxyl, halogen, C1-C6 alkyl, C1-C6 alkoxy, and C1-C6 hydroxyalkyl; each $R^2$ group is independently selected from H and C1-C6 alkyl; the $R^3$ group is selected from n-hexyl, n-heptyl, n-octyl, n-nonyl, n-decyl, undecyl, and dodecyl; and X is a halogen; and
   wherein a weight ratio of the graphite oxide to the total amount of the amine compound represented by formula (3) and the epoxy compound represented by formula (4) is 1: 48-250.

8. The method according to claim 7, wherein X is Cl or Br; each $R^1$ group is independently selected from H, hydroxyl, halogen, C1-C4 alkyl, C1-C4 alkoxy, and C1-C4 hydroxyalkyl; each $R^2$ group is independently selected from H and C1-C4 alkyl.

9. The method according to claim 8, wherein each $R^1$ group is independently selected from H, hydroxyl, methyl, ethyl, methoxy, ethoxy, hydroxymethyl, and hydroxyethyl; each $R^2$ group is independently selected from H, methyl, ethyl, n-propyl, and n-butyl.

10. The method according to claim 9, wherein each $R^1$ group is independently selected from H, methyl, and ethyl; each $R^2$ group is independently selected from H, methyl, ethyl, n-propyl, and n-butyl; and the $R^3$ group is selected from n-hexyl, n-heptyl, n-octyl, n-nonyl, and n-decyl.

11. The method according to claim 7, wherein the amine compound represented by formula (3) is selected from one or more of N,N-dimethyl tetradecylamine, N,N-dimethyl pentadecylamine, N,N-dimethyl hexadecylamine, N,N-dimethyl heptadecylamine, and N,N-dimethyl octadecylamine; and wherein the epoxy compound represented by formula (4) is epoxy chloropropane.

12. The method according to claim 7, wherein a molar ratio of the amine compound represented by formula (3) to the epoxy compound represented by formula (4) is 1.5-5:1.

13. The method according to claim 7, wherein the acid is one or more of hydrochloric acid, hydrobromic acid, and hydroiodic acid; and
wherein the solvent is one or more of methanol, ethanol, n-propanol, isopropanol, n-hexane, liquid paraffin, and methyl benzene.

14. The method according to claim 7, wherein the reaction is carried out at a temperature of 60-110° C. for a time of 12-24 hours.

15. An oil-based drilling fluid containing the lubricant according to claim 1.

16. The oil-based drilling fluid according to claim 15, wherein based on 100 part by weight of oil phase in the drilling fluid, the content of the lubricant is 5 part by weight or less.

17. The lubricant according to claim 1, wherein a weight ratio of the graphite oxide to the biquaternary ammonium salt compound is 1: 90-200.

* * * * *